US00PP28059P2

(12) United States Plant Patent
Hoogenraad

(10) Patent No.: US PP28,059 P2
(45) Date of Patent: May 30, 2017

(54) ***PHYSOCARPUS* PLANT NAMED 'HOOGI018'**

(50) Latin Name: *Physocarpus opulifolius*
Varietal Denomination: Hoogi018

(71) Applicant: Mark Sebastiaan Hoogenraad, Ederveen (NL)

(72) Inventor: Mark Sebastiaan Hoogenraad, Ederveen (NL)

( * ) Notice: Subject to any disclaimer, the term of this patent is extended or adjusted under 35 U.S.C. 154(b) by 57 days.

(21) Appl. No.: 14/756,843

(22) Filed: Oct. 21, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — Penny J. Aguirre

(57) ABSTRACT

A new cultivar of *Physocarpus opulifolius* plant named, 'Hoogi018', that is characterized by its very compact plant habit; reaching 40 cm in height as a four year-old plant in the landscape and its small size leaves that are gray-purple-red in color.

2 Drawing Sheets

Botanical classification: *Physocarpus opulifolius.*
Varietal denomination: 'Hoogi018'.

BACKGROUND OF THE INVENTION

The present invention relates to a new and distinct cultivar of *Physocarpus opulifolius* and will be referred to hereafter by its cultivar name, 'Hoogi018'. 'Hoogi018' represents a new cultivar of *Physocarpus*, a deciduous shrub grown for landscape use.

The new *Physocarpus* arose from a breeding program conducted by the Inventor in Ederveen, The Netherlands. The objective of the breeding program was to develop new *Physocarpus* cultivars with a compact plant habit.

The new *Physocarpus* originated from seed collected in 2008 and sown in 2009 from an open pollinated plant of *Physocarpus opulifolius* 'Monlo' (U.S. Plant Pat. No. 11,211). 'Hoogi018' was selected as a single unique plant from amongst 350 seedlings evaluated in 2012.

Asexual propagation of the new cultivar was first accomplished by stem cuttings by the Inventor in 2012 in Ederveen, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Hoogi018' as a unique and distinct cultivar of *Physocarpus.*

1. 'Hoogi018' exhibits a very compact plant habit; reaching 40 cm in height as a four year-old plant in the landscape.
2. 'Hoogi018' exhibits leaves that are gray-purple-red in color.
3. 'Hoogi018' exhibits small sized leaves.

'Monlo', the female parent of 'Hoogi018', differs from 'Hoogi018' in having a larger plant habit (reaching about 100 cm in height in four years in the landscape) and in having leaves that are larger and darker in color. 'Hoogi018' can also be compared to the cultivars 'Lady In Red' (U.S. Plant Pat. No. 18,660) and 'Hoogi021' (U.S. Plant patent application Ser. No. 14/756,840). 'Lady In Red' is similar to 'Hoogi018' in foliage color, however 'Lady In Red' differs from 'Hoogi018' in having a less compact plant habit and in having larger leaves. 'Hoogi021' is similar to 'Hoogi018' in having a very compact plant habit and small leaves. 'Hoogi021' differs from 'Hoogi018' in having leaves that are green and suffused with black in color.

BRIEF DESCRIPTION OF THE DRAWINGS

The accompanying colored photographs illustrate the overall appearance and distinct characteristics of the new *Physocarpus*. The photographs were taken of a plant 18 months in age as grown outdoors in a 12.5 cm container in Ederveen, The Netherlands.

The photograph in FIG. 1 provides a side view of the plant habit of 'Hoogi018'.

Figure 1:
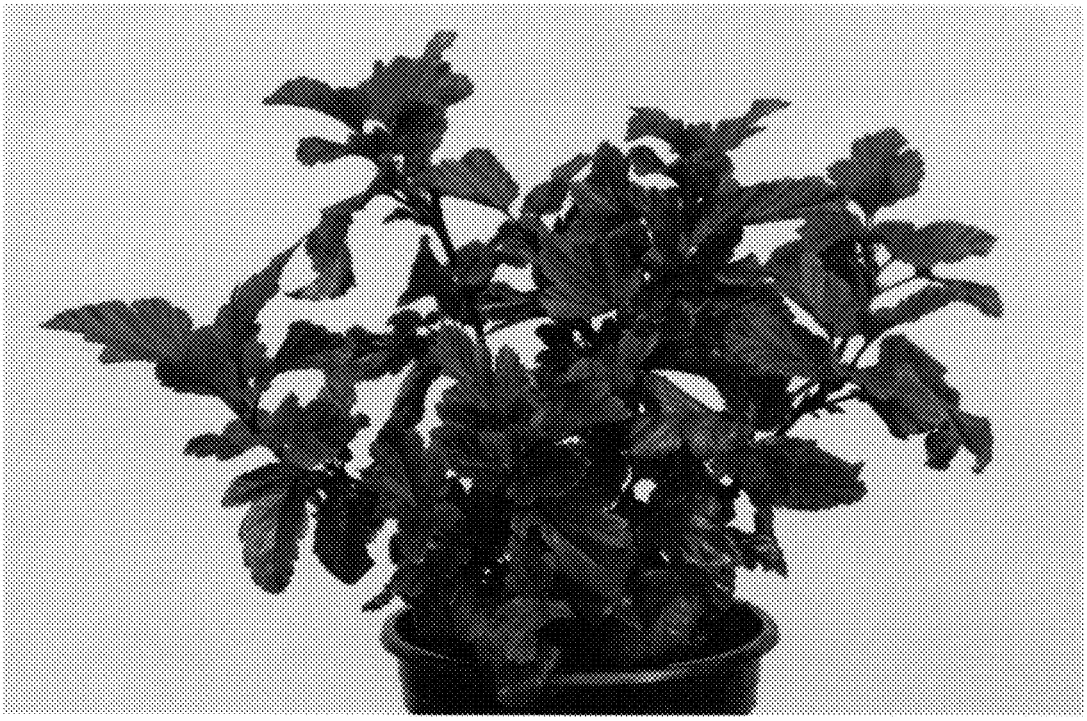
Figure 2:
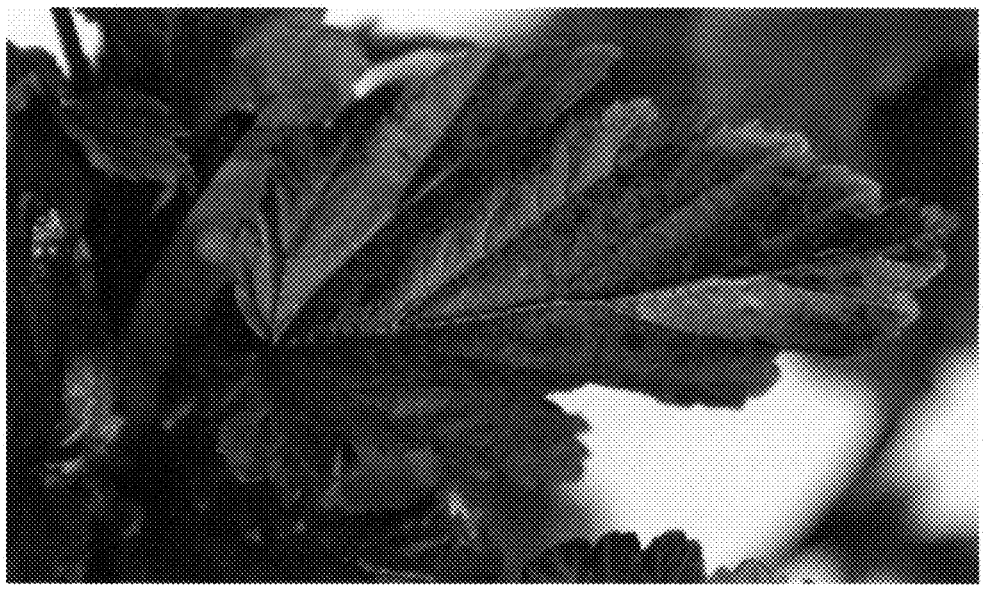

The photograph in FIG. 2 provides a close-up view of the upper surface a leaf of 'Hoogi018'.

Figure 3:
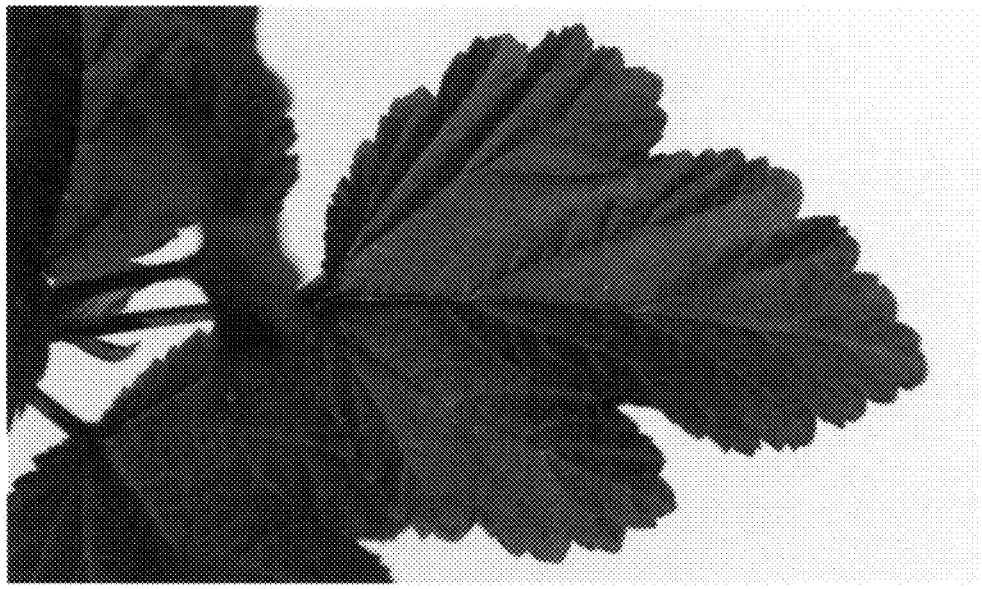

The photograph in FIG. 3 provides a close-up view of the upper and lower surface of leaves of 'Hoogi018'.

The colors in the photographs are as close as possible with the digital photography and printing techniques utilized and the color codes in the detailed botanical description accurately describe the colors of the new *Physocarpus.*

BOTANICAL DESCRIPTION OF THE PLANT

The following is a detailed description of 18 month-old plants of the new cultivar as grown outdoors in 12.5 cm containers in Ederveen, The Netherlands.mnPhenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General Description:

*Blooming period*.—No flowers observed to date.

*Plant type*.—Perennial shrub.

*Plant and growth habit*.—Very compact, mounded shape.

*Height and spread*.—An average of 21.3 cm in height and 31.3 cm in spread as grown in a 12.5 cm container, reaches 4.0 cm in height and 50 cm spread in 4 years when grown in the landscape.

*Cold hardiness*.—At least to U.S.D.A. Zone 3.

*Diseases and pest resistance*.—Similar susceptibility and resistance to diseases and pests to other *Physocarpus* cultivars.

*Root description*.—Fibrous and fine.

Growth and propagation:

*Growth rate*.—Slow to moderate.

*Propagation*.—Softwood stem cuttings.

*Root development*.—An average of 4 weeks to produce a rooted cutting and about 12 months weeks to produce a fully rooted plant in a 12.5-cm container.

Branch description:

*Branch color*.—New wood; a blend between 184A to 185A, older bark; 200B with exfoliating bark a blend of 164A to 164B and 165B.

*Branch size*.—An average of 11 cm in length and 2.5 mm in diameter.

*Number of lateral branches*.—An average of 9 per plant.

*Branch surface*.—Slightly glossy.

*Branch shape*.—Rounded and slightly angled.

*Branch internode length*.—An average 1.7 cm.

*Branch habit*.—Freely branching, lateral branches emerge from the base of main stems.

*Branch strength*.—Strong.

Foliage description:

*Leaf shape*.—Ovate in outline, deeply tri-lobed, maple-like.

*Leaf division*.—Simple.

*Leaf base*.—Truncate to cordate.

*Leaf apex*.—Acute.

*Leaf venation*.—Pinnate, color; upper surface N200A suffused with 147A and lower surface 181B.

*Leaf margin*.—Tri-lobed and biserrate.

*Leaf attachment*.—Petiolate.

*Leaf arrangement*.—Alternate.

*Leaf surface*.—Both surfaces glabrous, upper surface moderately glossy and lower surface dull.

*Leaf size*.—An average of 6 cm in length and 5.3 cm in width.

*Leaf number*.—About 7 per lateral branch.

*Leaf color*.—Young foliage; upper surface a blend between N186C and 200B, lower surface 199B suffused with 177B, mature foliage; upper surface N200A suffused with 147A, lower surface N200A suffused with 148A.

*Petiole*.—Flattened in shape, an average of 1.6 cm in length, 1 mm in width, and 1.5 mm in height, 187B in color.

*Stipules*.—2 present at the base of each petiole, obovate to oblong in shape, acute tip, broadly cuneate base, an average of 7 mm in length and 3.5 mm in width, color; upper and lower surface 180C to 180D with veins 185A to 185B, dropped when leaves mature.

Flower description: No flowers observed to date.

It is claimed:

1. A new and distinct cultivar of *Physocarpus* plant named 'Hoogi018' substantially as herein illustrated and described.

* * * * *